(12) United States Patent
Kutchinski

(10) Patent No.: US 12,138,290 B2
(45) Date of Patent: Nov. 12, 2024

(54) MICRO-FOG ANTI PATHOGENIC COMPOSITION AND METHOD OF PREPARATION

(71) Applicant: David Paul Kutchinski, Larkspur, CO (US)

(72) Inventor: David Paul Kutchinski, Larkspur, CO (US)

( * ) Notice: Subject to any disclaimer, the term of this patent is extended or adjusted under 35 U.S.C. 154(b) by 178 days.

(21) Appl. No.: 17/138,221

(22) Filed: Dec. 30, 2020

(65) Prior Publication Data

US 2022/0202891 A1 Jun. 30, 2022

(51) Int. Cl.
| | |
|---|---|
| *A61K 36/53* | (2006.01) |
| *A61K 35/644* | (2015.01) |
| *A61K 36/00* | (2006.01) |
| *A61K 36/185* | (2006.01) |
| *A61K 36/24* | (2006.01) |
| *A61K 36/315* | (2006.01) |
| *A61K 36/484* | (2006.01) |
| *A61K 36/537* | (2006.01) |
| *A61K 36/539* | (2006.01) |
| *A61K 36/71* | (2006.01) |
| *A61K 36/9068* | (2006.01) |
| *A61K 47/02* | (2006.01) |

(52) U.S. Cl.
CPC ............ *A61K 36/53* (2013.01); *A61K 35/644* (2013.01); *A61K 36/185* (2013.01); *A61K 36/24* (2013.01); *A61K 36/315* (2013.01); *A61K 36/484* (2013.01); *A61K 36/537* (2013.01); *A61K 36/539* (2013.01); *A61K 36/71* (2013.01); *A61K 36/9068* (2013.01); *A61K 47/02* (2013.01)

(58) Field of Classification Search
None
See application file for complete search history.

(56) References Cited

U.S. PATENT DOCUMENTS

| | | | | |
|---|---|---|---|---|
| 5,357,636 | A * | 10/1994 | Dresdner, Jr. ...... | A41D 19/0096 2/167 |
| 2021/0386811 | A1* | 12/2021 | Tatch ..................... | A61K 36/45 |
| 2022/0370309 | A1* | 11/2022 | Summers ............... | A61K 8/735 |

* cited by examiner

*Primary Examiner* — Aaron J Kosar
*Assistant Examiner* — Randall O Winston
(74) *Attorney, Agent, or Firm* — Yonaxis I.P. Law Group; Brent T. Yonehara

(57) ABSTRACT

The present invention relates to developing a plant-based composition for arresting the spread of pathogens from an infected person which can be sprayed in infected places, for rapidly decontaminating the affected areas thereby arresting the spread in larger areas which includes include, office complexes, hospitals, schools, mass transportation, prisons, care facilities, public housing, and mass transportation terminals. The present composition is a mixture containing herbs including lavender, Chinese skullcap, black seed oil, *Sida acuta, cryptolepis, Isatis*, licorice, sage, medicinal honey and ginger in a colloidal silver base.

3 Claims, No Drawings

MICRO-FOG ANTI PATHOGENIC COMPOSITION AND METHOD OF PREPARATION

FIELD OF THE INVENTION

The present invention relates to an anti-pathogenic formulation capable of being pulmonary administered which can be distributed to the lungs and which decreases the infectivity, morbidity and rate of mortality associated with a variety of pathogens. The present invention more particularly relates to plant based formulations and methods for decontaminating areas, samples, solutions and also in arresting the vectors of pathogens in infected individuals from a potential outbreak and which can be distributed mechanically through micro fogging methods.

BACKGROUND OF THE INVENTION

There is a growing demand for infection control and enhanced cleaning services. As a society we are now all too aware of the risks posed by various infections and by less regular but potentially lethal swine, bird flu and corona virus pandemics. At times of heightened risk, hand sanitizers moved from hospital entrances into corporate offices, and are now increasingly commonplace.

Usually, most pathogens require vectors (such as humans) to multiply and spread. Also, some viruses, can spread directly through close contact, for example if an infected person is in close contact with a healthy, there are high chances of contracting the pathogenic virus. Further the pathogens may spread though indirect contact as well. Indirect contacts may include droplet infection through surface contamination where the pathogens may survive for many days. Once these surfaces are touched by human, they become probable vectors of transmission.

To arrest the spread of such pathogens, many chemical formulations have been developed which can be sprayed in areas such as hospitals, public transport systems, offices, institutions etc., but a disadvantage lies in such formulations, that they can be harmful to the human as well as animals if present in that specific area. Hence before spraying, these areas need to be evacuated and cannot be used for a period.

Another, disadvantage, of such formulations are that with time, these chemical formulations become ineffective on the targeted pathogen. This is since pathogens constantly mutate and develop resistance towards these formulations.

Further, most of these formulations are pathogen specific, i.e. they are effective towards few groups of pathogens.

To overcome the above disadvantages of the present formulations, the need is to develop a plant based formulation, which are effective towards most pathogens are not only harmless to the humans and animals, but if inhaled by any infected person, helps in arresting the spread of the pathogen.

SUMMARY OF THE INVENTION

An aspect of the invention is to develop mostly plant-based formulations for arresting the spread of pathogens in an infected person.

Another aspect of the invention is to develop mostly plant-based formulations which can be sprayed in infected places, for rapidly decontaminating the affected areas thereby arresting the spread in larger areas. These areas may include, office complexes, hospitals, schools, mass transportation, prisons, care facilities, public Housing, and mass transportation terminals.

An aspect of the present invention is to develop a plant-based formulation, wherein the DNA or RNA of pathogens cannot develop resistance towards it and hence the formulation can be effective over longer duration of time.

In another aspect of the present invention, the formulations are nontoxic and non-allergic and may be safely ingested by humans and other animals.

In still another aspect of the present invention, the affected person can be contacted with effective amounts of the compositions after exposure to pathogenic organisms, for boosting the immune system and arresting the spread of the pathogen.

In another aspect of the present invention, the formulation can be deployed through sprays and therefore the formulation may be ingested through the lungs which has an advantage of quickly diffusing into the blood cells, thereby the time taken to arrest the pathogen is very less.

In another aspect of the present invention, the invention provides compositions and methods suitable for decontaminating hospitals, schools, mass transportation, prisons, care facilities, public housing and mass transportation terminals that are exposed to pathogens or suspected of containing pathogens through microfogging.

In still further aspect of the present invention, the formulation is a mixture containing herbs including lavender, Chinese skullcap, black seed oil, *Sida acuta, cryptolepis, Isatis*, licorice, sage, medicinal honey and ginger in a colloidal silver base.

DESCRIPTION OF THE PREFERRED EMBODIMENT

It should be understood at the outset that, although exemplary embodiments have been described below, the principles of the present disclosure may be implemented using any number of techniques, whether currently known or not. The present disclosure should in no way be limited to the exemplary implementations and techniques described below.

Microfogging:

The present invention uses the technique of micro-fogging for application of the present formulation over large areas to ensure full coverage of the infected area. Biofogging has been around a long time as a way of sanitising interior spaces in buildings and since, the prior disadvantages of being harmful or toxic to humans and animals have been overcome in this invention, mass micro-fogging of the entire affected space can be easily undertaken.

Micro fogging produces a fine mist or fog depending upon the area of the formulation of the present invention. The formulation or the biocide particles in the mist or fog are very small to the size less than 100 Microns, so that they remain suspended in the air long enough to kill airborne viruses and bacteria. The biocide also eliminates pathogens on surfaces, including ceilings and walls as well as furniture and floors.

Since micro fogging further enables the formulation to reach areas that may be difficult to clean with other techniques. Penetration into some nooks and crannies may be limited by obstacles, but in the present invention it is not necessary to move furniture or equipment around before or during the fogging process.

Another advantage of the formulation of the present invention, is such that if ingested through lungs, by the infected person, it functions to arrest the spread of the pathogen in the lungs, which helps in fast diffusion into the blood cells thereby helping in arresting or curing the individual of the pathogenic infestation.

Pulmonary Administration of Drugs

The formulation of the present invention is devised to be ingested through lungs by the affected individuals. Since, the efficacy of a treatment mostly depends on the techniques by which the drug is delivered; pulmonary delivery of drug is the most effective way of infusing any drug as the lung is capable of absorbing pharmaceuticals either for local deposition or for systemic delivery. The respiratory epithelial cells have a prominent role in the regulation of airway tone and the production of airway lining fluid. Due to the high permeability and large absorptive surface area of lungs, (approximately 70-140 m2 in adult humans having extremely thin absorptive mucosal membrane) and good blood supply, the alveolar epithelium of the distal lung has been shown to be an absorption site for most of the therapeutics and various macromolecules. Further advantages over peroral applications are the comparatively low enzymatic activity, rapid absorption of drug and the capacity for overcoming first-pass metabolism.

Composition

Note: ALL herbs used in this process possess a COA stating that the plant has been tested for heavy metal, bacteria count and pesticide residue.

Many forms of extraction are used, the easiest and cheapest is solvent extraction using alcohol, but the steam distillation method is used in this patent whenever available.

LAVENDER (*Lavandula augustifola*):

Lavender oil has anti-bacterial and anti-fungal properties mainly due to the presence of main components such as 1.8-cineol, linalool, linalyl acetate, lavandulol, geraniol, or eucalyptol. It works by destroying the membranes of fungal cells and shows antifungal activity on a wide spectrum.

The oils of the Lavender are used. The flowers, although fragrant, do not have the efficacy of the extracted oils of the plant.

CHINESE SKULLCAP (*Scutellaria baicalensis*).

The roots of the Chinese Skullcap and ONLY the roots are used. Additionally, the roots used in this formulation are from plants older than 3 years old.

As the name suggests, Chinese skullcap, or scientifically called *Scutellaria baicalensis*, is the golden herb from the garden of Chinese medicinal plants. It contains an array of beneficial plant compounds, including antioxidants, which have anti-inflammatory effects and protect cells from damage caused by molecules called free radicals. Used for CNS damage or encephalitis. The root is high in melatonin, so it can help with sleep.

Various parts of *S. baicalensis* extracts have has substantial antibacterial, antimycotic properties against many foods borne pathogens. Further it also enhances the antimicrobial activity of several antibiotics against.

*Scutellaria baicalensis* produces various natural products including amino acids, essential oils, flavonoids, phenylethanoids, and sterols. More than 30 types of flavones can be found in its roots (FIG. 3), including baicalin, baicalein, chrysin, oroxylin A, oroxylin A 7-O-glucuronide, wogonin and wogonoside. Baicalin, baicalein, wogonin, and wogonoside are the major bioactive compounds extracted from *S. baicalensis*.

BLACK SEED OIL (*Nigella sativa*):

Part of the Ranunculacea family. The seeds of the *Nigella sativa* and ONLY the seeds are used.

*Nigella sativa* has antioxidant, immune-boosting, anti-inflammatory, anti-tussive, anti-hypertensive, anti-diabetic, antibacterial, and anti-cancer properties.

The key reason for using this herb is its critical need in stopping the Cytokine storm that fills the lungs with fluid that ends up killing the host. Specifically, the TGF-β2 Cytokine which creates the over production of mucus and lung tissue inflammation.

SIDA ACUTA: *Sida acuta* is Belongs to the Family Malvaceae.

The parts of the plant used: the whole plant but readily available forms of the herb are mainly from the aerial parts.

It has many pharmacological applications including antiplasmodial, antibacterial, antifungal, antioxidant, cytotoxic and many other properties. Apart from these the plant possess various other pharmacological activities like antiviral, antiplasmodial, anti-inflammatory, anti-oxidant, analgesic, anti-ulcer, hypoglycemic, antipyretic, hepatoprotective, and wound healing properties. Due to the presence of phytochemicals, tannins, saponins, alkaloids, flavonoids, terpenes andphenolics in *S. Acuta*, it has the above medicinal properties. And can be used for a wide variety of treatments.

The key aspect of the use of *Sida acuta* in this formulation is for its anti-bacterial effects on wounds, *E. coli*, Bacillus. It has also been used for eye infections, Malaria, sepsis in wounds, staph infections (MRSA), *Shigella*, and TB.

CRYPTOLEPIS: Part of the Apocynaceae Family.

The root of the Cryptolepis are used. Effective herb against TB, UTI and wound sepsis. Tests have found the plant to be a stronger antibacterial than the pharmaceutical antibiotic chloramphenicaol. Broadly active against Gram-Positive bacteria {MRSA, *C. Diff*, pyogenic infections (pharyngitis, cellulitis, impetigo, erysipelas), toxigenic infections (scarlet fever, necrotizing fasciitis), and immunologic infections (glomerulonephritis and rheumatic fever)} but is potent against a number of Gram-negative bacteria {*E. coli*, Cholera, Plague, *Salmonella*}. Additionally, it is included for its anti-fungal {*Candida*}.

ISATIS (*Isatis tinctoria*): Part of the Brassicaceae family.

The root and leaves of the *Isatis* are used.

*Isatis* is the MVP of the mix for effective actions against ALL influenza viruses SARS and all primary respiratory virus infections, Epstein-Barr, Shingles, conjunctivitis, parvovirus.

In addition to the effectiveness against SARS-type it also has antimicrobial actions against MRSA, *C. diff*, *E. coli candida*.

The *Isatis* species has antibacterial, anticancer, and antiviral properties and these important endemic plants grow widely in various parts of Anatolian-Turkey. The above properties are because the leaves and roots of *Isatis* are shown to have a wide variety of compounds.

The leaf extracts of some species of Isatislike *Isatis tinctoria* have been shown to have more than 65 compounds belonging to various structural classes such as alkaloids, flavonoids, fatty acids, porphyrins, lignans, carotenoids, glucosinolates and cyclohexenonesand indolic alkaloid.

The root extracts of *Isatis indigotica* Fort (ROCIIT) is a commonly used traditional Chinese medicine for anti-inflammatory remedies. Apart from being used as anti-inflammatory agent, the roots of *I. indigotica* also contains compounds like arginine, cytidine, tyrosine, uridine, phenylalanine, guanosine, goitrin, adenosine, isaindigodione, salicylic acid, indigoticalignanoside A, and hydroxyindirubin, were identified.

LICORICE (*Glycyrrhiza glabra*): Part of the Leguminosae family.

The root of the Licorice is used. The choice of using Licorice in this formula was primarily due to its action in increasing the efficacy of the herbs chosen to combat the Cytokine Storm in the lungs. In addition, it is a key element in fighting the storm as it inhibits viral growth, viral uptake, inactivates virus particles, strongly inhibits viral cytokine cascades, stops the ballooning degeneration of fused cells, inhibits RANTES secretion. BOTTOM LINE: It stops the virus-induced development of membrane pores through which the viruses can enter the host cells.

The main ingredients glycyrrhizin (GL), 18β-glycyrrhetinic acid (GA), liquiritigenin (LTG), licochalcone A (LCA), licochalcone E (LCE) and glabridin (GLD) are the main active components which possess antiviral and antimicrobial activities.

SAGE (*Salvia officinalis*):

The genus *Salvia*, commonly known as sage, is the largest member of Lamiacea or mint family. The leaves and stems of the Sage are used.

In species *S. officinalis*, the major components, although, present in different concentrations, are: 1,8-cineole, camphor, borneol, bornyl acetate, camphene, α- and β-thujone, linalool, α- and β-caryophyllene, α-humulene, α- and β-pinene, viridiflorol, pimaradiene, salvianolic acid, rosmarinic acid, carnosolic acid, ursolic acid, etc.

Sage is also a natural source of flavonoids and polyphenolic compounds (e.g., carnosic acid, rosmarinic acid and caffeic acid) possessing strong antioxidant, radical-scavenging, and antibacterial activities. Research suggests it can be effective against airborne microorganisms, treat wounds and skin infections caused by *staphylococcus*.

Medicinal Honey:

Honey is a sweet and flavorful natural product, which is high in nutritive value and has positive effects on human health due to its antioxidant, bacteriostatic, anti-inflammatory and antimicrobial properties.

The "clinical honey" accepted by the USFDA is from New Zealand that is called Manuka which is from the flowers of *Leptospermum scoparium* (aka "Manuka) which is a type of Tea tree.

The fact is that ANY wildflower honey will work. Extensive research has discovered that many large honey producers have hives in the wild. The more plants the bees use, the more potent the honey for medicinal purposes.

It promotes healing of wounds. Potent anti-biotic against ALL form of resistant bacteria. It also soothes inflamed tissue; acts as a wound barrier; burns ($1^{st}$ through $3^{rd}$ degree) and stimulates skin and muscle regeneration.

The main reason for using this herb is that it is sticky. To increase the time of efficacy of the formula it needs a way to stay together, stick to what it lands on and evaporate slowly. To spray the formula into the mouth or breathe it in, it must taste decent. And hence honey is used.

GINGER (*Zingiber officinale*): A member of the Zingiberaceae family.

The major constituents in ginger rhizomes are carbohydrates (50-70%), lipids (3-8%), terpenes, and phenolic compounds. Terpene components of ginger include zingiberene, β-bisabolene, α-farnesene, β-sesquiphellandrene, and α-curcumene, while phenolic compounds include gingerol, paradols, and shogaol. These gingerols (23-25%) and shogaol (18-25%) are found in higher quantity than others. Besides these, amino acids, raw fiber, ash, protein, phytosterols, vitamins (e.g., nicotinic acid and vitamin A), and minerals are also present.

As an antiviral, ginger inhibits the attachment of viruses to the cell, inhibits hemagglutinin, inhibits viral proteases, inhibits neuraminidase, stimulated antiviral macrophage activity and very virucidal.

Process:

The formulation of the present invention is Colloidal Silver (10-20 PPM at ≈0.0008-micron silver particle size) based. The methodology of making the Colloidal Silver uses a meter to constantly monitor the micro siemens vs. the traditional guesswork based on firing a laser through the solution.

The exact proportions of each element of the formula is what took the longest time to determine. If one element ratio to another is off, then the formula, as a whole will be less than effective, if at all.

The steps of preparing the formulation, comprises:

Adding the following herbs to a colloidal silver base in a clean room with no direct sunlight:

All number below are percentage of volume:
Lavender (*Lavandula augustifola*); 0.09
Chinese Skullcap (*Scutellaria baicalensis*); 0.13
Black Oil (*Nigella sativa*); 0.09
*Sida Acuta*; 0.11
Cryptolepis; 0.12
*Isatis* (*Isatis tinctoria*); 0.13
Licorice (*Glycyrrhiza glabra*); 0.18
Sage (*Salvia officinalis*); 0.51
Medicinal Honey; 4.68
Ginger (*Zingiber officinale*); 0.18
Colloidal Silver; 93.78

Upon addition of all the ingredients to the colloidal silver base, increasing the admixed compound mixture with ≥30% hydrogen peroxide ($H_2O_2$) solution at a slow rate of 45 RPM, thereby acting as a binding agent to ensure the admixed compound is mixed; and Stirring the room temperature mixture at (75° F./24° C.) by using a magnetic stirrer such as the Genie SI-0300 MagStir for ≥24 hours.

The synergistic composition, thus obtained by the above method and having the above composition, when microfogged over large areas, ensures full coverage of the infected area.

It is to be understood that the aforementioned components and volumes as well as steps are only exemplary and that various arrangements are possible in other embodiments. While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings.

The embodiments discussed were chosen and described to provide the best illustration of the principles of the invention and its practical application to enable one of ordinary skill in the art to utilize the invention in various embodiments and with various modifications as are suited to the particular use contemplated. All Such modifications and variations are within the scope of the invention as determined by the appended claims when interpreted in accordance with the breadth to which they are entitled.

The invention claimed is:

1. A method of producing an anti-pathogenic composition, comprising the method steps of:

a. admixing components to form a formulation as a solution comprising by weight percent of the solution of 0.06% *Lavandula augustifola*, 0.08% *Scutellaria baicanlensis*, 0.11% *Nigella sativa*, 0.09% *Sida Acuta*, 0.08% *Cryptolepsis*, 0.08% *Isatis tinctoria*, 0.11% *Glycyrrhiza glabra*, 0.07% *Salvia officinalis*, 2.89% medicinal honey, and 0.12% *Zingiber officinale*, and a colloidal silver base;

b. increasing the admixed component mixture with ≥30% hydrogen peroxide solution at a rate of 45 RPM; and c. stirring the admixture of step (a) at room temperature by using a magnetic or electric overhead stirrer.

2. The method of claim 1, wherein the solution comprises by weight percent of 96.3% colloidal silver base.

3. The method of claim 1, wherein the admixture mixture of step (c) is stirred by the magnetic or electric overhead stirrer for 24 hours.

\* \* \* \* \*